United States Patent [19]

Kurwa

[11] Patent Number: 4,574,804
[45] Date of Patent: Mar. 11, 1986

[54] OPTIC NERVE CLAMP

[75] Inventor: Badrudin Kurwa, Galveston, Tex.

[73] Assignee: Board of Regents, The University of Texas System, Austin, Tex.

[21] Appl. No.: 583,764

[22] Filed: Feb. 27, 1984

[51] Int. Cl.⁴ ............................................. A61B 17/28
[52] U.S. Cl. ................................. 128/322; 128/325; 128/346; 81/418
[58] Field of Search .................. 128/303 R, 322, 321, 128/325, 354, 346, 340; 81/418, 426

[56] References Cited

U.S. PATENT DOCUMENTS

| | | |
|---|---|---|
| 1,852,542 | 4/1932 | Sovatkin . |
| 1,918,889 | 7/1933 | Bacon . |
| 2,668,538 | 2/1954 | Baker . |
| 2,796,065 | 6/1957 | Kapp . |
| 2,887,111 | 5/1959 | Diaz ................................. 128/321 |
| 2,962,024 | 11/1960 | Raymond . |
| 3,515,139 | 6/1970 | Mallina . |

FOREIGN PATENT DOCUMENTS

| | | | |
|---|---|---|---|
| 106809 | 7/1927 | Austria . | |
| 256535 | 2/1913 | Fed. Rep. of Germany . | |
| 160270 | 3/1964 | U.S.S.R. | 128/321 |
| 162284 | 4/1964 | U.S.S.R. | 128/303 R |

OTHER PUBLICATIONS

American V. Mueller Surgical Instruments Catalog (1980), p. 567.

Primary Examiner—Michael H. Thaler
Attorney, Agent, or Firm—Arnold, White & Durkee

[57] ABSTRACT

An optic nerve clamp, useful for surgical enucleation includes a pair of clampingly abutting, pivotally connected jaws with tip portions which curve out of the plane perpendicular to and extending through the pivot axis of said jaws. One of the tip portions is longer than the other so that an offset is formed between their tapered ends. The region of overlap between the two tip portions is serrated but the extension of the longer tip portion beyond the shorter tip portion is substantially smooth.

9 Claims, 9 Drawing Figures

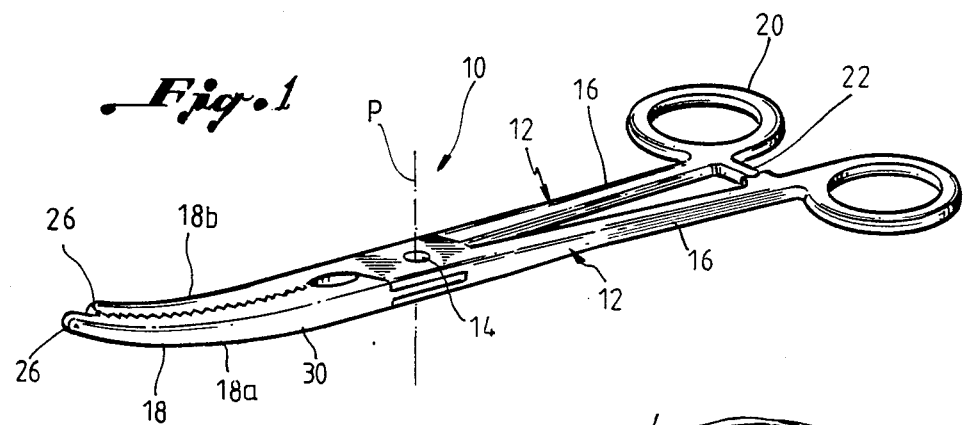
Fig. 1
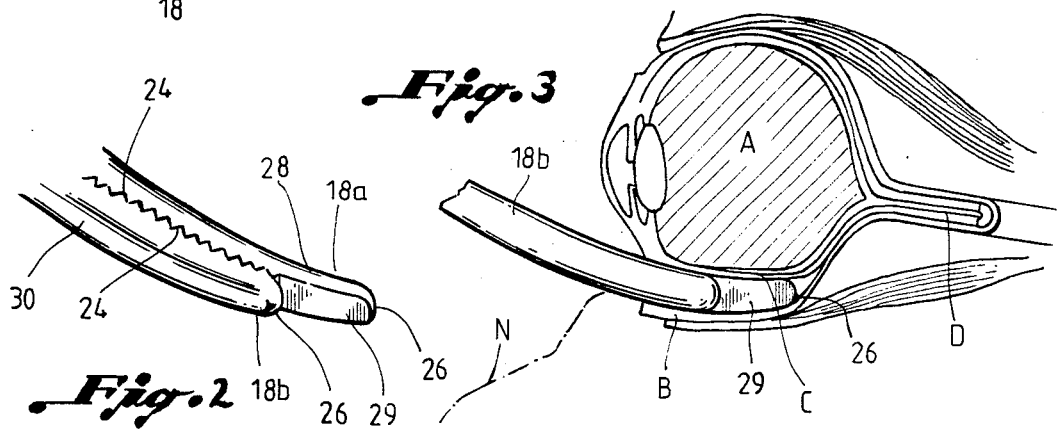
Fig. 2  Fig. 3
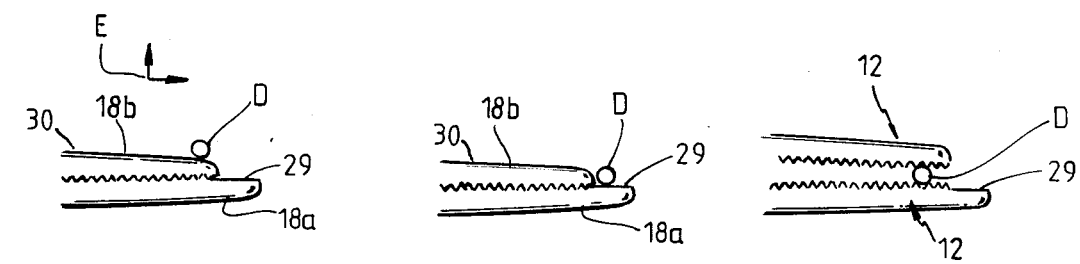
  
Fig. 4b  Fig. 5b  Fig. 6b
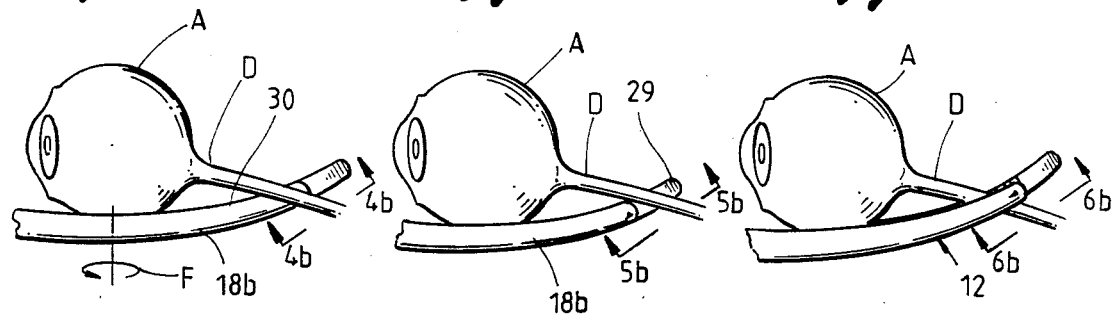
  
Fig. 4a  Fig. 5a  Fig. 6a

OPTIC NERVE CLAMP

BACKGROUND OF THE INVENTION

1. Field of the Invention

This invention relates generally to the field of medical instruments and specifically to a means for clamping the optic nerve during enucleation.

2. Background Art

During enucleation, the removal of a diseased eyeball, the optic nerve is usually clamped to insure hemostasis and to facilitate excision of a long segment of the optic nerve. In the past, this process of clamping the optic nerve during enucleation has been done blindly, by feel, with a hemostat. The disadvantage of this procedure has been uncertainty as to the extent and type of tissue in the clamp.

Unintended excision of large amounts of surrounding tissue can occur occasionally and, rarely, rupture of the eyeball itself can occur if great care is not exercised when using conventional equipment. A large loss of tissue behind the eyeball globe can cause secondary problems including prosthesis migration.

It would be highly desirable to have a surgical instrument which facilitates the clamping of the optic nerve and particularly an instrument which allows isolation of the nerve. Further, it would be desirable to have an instrument which decreases the possibility of inadvertent excision in the back part of the eyeball and which reduces the likelihood of damage to the surrounding tissue. In addition, it would be highly desirable to provide a surgical instrument that allows for positive identification of the optic nerve before clamping.

SUMMARY OF THE INVENTION

These and other objects of the present invention may be achieved by an optic nerve clamp that includes a pair of clamping jaws connected at a pivot for relative movement about a pivot axis extending through the pivot. Each of the jaws has a tip portion on one side of the pivot and a handle portion on the opposite side of the pivot. The tip portions, arranged to clampingly abut with one another, are curved to extend out of the plane perpendicular to the pivot axis. One of the tip portions is shorter than the other such that the ends of the tip portions are offset.

In accordance with another embodiment of the present invention, an instrument is provided for surgical enucleation. The instrument includes a pair of clamping jaws connected at a pivot for relative movement about a pivot axis extending through the pivot. Each of the jaws has a tip portion on one side of the pivot and a handle portion on the opposite side of the pivot. The tip portions, arranged to clampingly abut with one another, are curved sufficiently to allow access to the optic nerve around the eyeball. The curved portions extend out of the plane perpendicular to the pivot axis. One of the tip portions is shorter than the other such that the ends of the tip portions are offset. The end of the longer tip portion is tapered sufficiently to allow the instrument to be inserted between the sclera and the Tenon's capsule. The offset of the tip portions is adapted to permit the optic nerve to be located between the end of the shorter tip portion and the section of the longer tip portion extending beyond the shorter tip portion.

BRIEF DESCRIPTION OF THE DRAWINGS

FIG. 1 is a perspective view of one embodiment of the present invention;

FIG. 2 is a partial, enlarged perspective view of the end portions of the instrument shown in FIG. 1;

FIG. 3 is a partial top plan view of the end portions of the instrument, shown in FIG. 1, inserted within the human eye socket viewed in a horizontal crosssection;

FIG. 4a is a partial top plan view, similar to that shown in FIG. 3, but with the surrounding tissues removed and the instrument having been inserted into the region adjacent the optic nerve;

FIG. 4b is a partial cross-sectional view taken generally along the line b—b in FIG. 4a;

FIG. 5a is a view similar to that of FIG. 4a but with the surgical instrument in a different position relative to the optic nerve;

FIG. 5b is a partial cross-sectional view taken generally along the line b—b in FIG. 5a;

FIG. 6a is a view similar to that of FIG. 5a but with the surgical instrument in a different position relative to the optic nerve; and FIG. 6b is a partial cross-sectional view taken generally along the line b—b in FIG. 6a.

DETAILED DESCRIPTION OF THE PREFERRED EMBODIMENT

Referring to the drawing wherein like reference characters are used for like parts throughout the several views, the optic nerve clamp 10, shown in FIG. 1, includes a pair of pivotally connected, clampingly abutting jaws 12. The jaws 12 are connected for relative pivotal movement about a pivot axis "P" extending through and parallel to the pivot pin 14. A pair of handle portions 16 are defined on one side of the pivot pin 14 and a pair of tip portions 18 are defined on the opposite side.

The handle portions 16 are arranged in a conventional format with a pair of looped finger engaging ends 20 arranged to be manually operable by human fingers. The looped ends 20 are connectable by a catch 22 which allows the handle portions 16 to be releasably locked together, in a conventional fashion.

The tip portions 18 may have broadly flat, abutting, serrated facing surfaces 24, as shown in FIGS. 1 and 2, and curved opposite surfaces 30. The surfaces 30 may taper in thickness gently towards one another as they extend away from the pivot 14. The tip portions 18 also may narrow in width as they extend away from the pivot 14. Moreover, the tip portions 18 are curved so that they extend out of the plane perpendicular to the pivot axis of the jaws 12. More particularly, the tip portions 18 advantageously lie in a plane parallel to the length of the clamp 10 and substantially perpendicular to the plane of the handle portions 16. The ends 26 of the tip portions 18 are gently rounded and offset such that an extension 28 is defined in the tip portion 18a relaitive to the shorter tip portion 18b. The extension 28, advantageously approximately five millimeters in length, has a smooth flat surface 29 adjacent the tip portion 18b.

When the handle portions 16 are separated, the tip portions 18 are also separated but because of the curvature of the tip portions 18, the ends 26 move in a plane separate and distinct from the plane that includes the handle portions 16. This permits access to the region behind an eyeball so that the optic nerve can be grasped in a way explained hereinafter. More particularly, the curvature of the tip portions 18 is such that the ends 26 may be located at the optic nerve with the handle portions 16 extending tranversely away from the patient's face.

As shown in FIGS. 3 through 6, the optic nerve clamp 10 may be used to implement a surgical enucleation. After the extraocular muscles have been disinserted, the globe A, grasped at the insertion of the medial rectus muscle with two of the forceps (not shown), is pulled up and out of the socket. This maneuver puts some traction on the optic nerve.

The clamp 10 is then wedged, with the jaws 12 closed, between the sclera B and the Tenon's capsule C on the nasal side of the globe A (the patient's nose is labelled "N" in FIG. 3), with the ends 26 of the clamp 10 pointing in the direction of the optic nerve D, as indicated in FIG. 3. Thus, the tip portions 18 are inserted with the pivot axis of the clamp 10 arranged in generally a horizontal plane with the patient's head resting on a surgical table.

The upper surface 30 of the shorter tip portion 18b is placed against the optic nerve, as indicated in FIGS. 4a and 4b. This positioning of the clamp 10 can be confirmed by observing whether inward and upward movements, indicated by the arrows E in FIG. 4b, produce small movements, indicated by arrow F in FIG. 4a, of the globe.

The clamp 10 is then pressed against the optic nerve continuously while being withdrawn, until the nerve is felt to slide off the end 26 of the shorter tip portion 18b, as shown in FIGS. 5a and 5b. The nerve now lies on the smooth surface 29 of the longer tip portion 18a. The jaws 12 of the clamp 10 are then opened and the clamp 10 is pushed in again until the nerve lies between the tip portions 18 of the clamp 10, as shown in FIGS. 6a and 6b. The nerve is then clamped. After the nerve is clamped, it can be easily severed with scissors just anterior to the clamp 10. The clamp 10 is left on for 5 to 10 minutes to facilitate hemostasis. Once the nerve is clamped and severed, and the globe is removed, the nerve stump and the edges of the posterior opening in the Tenon's capsule can be expected to facilitate later repair.

The clamp 10 acts as a guide to insure that the nerve is within its jaws 12. It also protects against accidental clamping and excision of the posterior portion of the globe because the extension 28 functions like a wedge that pushes itself into position behind the back wall of the sclera during the first insertion.

Because of the symmetry of the clamp 10, it is possible to curve the tip portions 18 in the direction shown on FIG. 1 or in the exact opposite direction. It may also be desirable to have two clamps 10 with opposite curvatures, such that one clamp 10 is used in connection with the left eye and the other is used in connection with the right eye. However one clamp 10 can, if desired, be used on both eyes by simply using the clamp 10 in the configuration shown in FIGS. 3-6 and then using it, for the other eye, in an up-side-down configuration compared to the illustrated orientation.

Surgeons will appreciate that the clamp 10 is not applicable to certain cases. For example, if a posterior scleral perforation is present, the longer tip of the clamp 10 may be inserted inadvertently into the globe. If an ocular malignancy exists, tumor cells may be squeezed along the nerve sheaths during the clamping process.

Although the present invention has been described with respect to a single preferred embodiment, those skilled in the art will appreciate a number of variations. It is intended within the appended claims to cover all such modifications and variations as come within the true spirit and scope of the present invention.

What is claimed is:

1. An optic nerve clamp comprising a pair of clamping jaws connected at a pivot for relative movement about a pivot axis extending through said pivot, each of said jaws having a tip portion on one side of said pivot and handle portion on the opposite side of said pivot, said tip portions, arranged to clampingly abut with one another, being curved to extend out of the plane perpendicular to said pivot axis, wherein the extent of curvature of said tip portions is precisely sufficient to enable access to the optic nerve from around the side of the eyeball, one of said tip portions being shorter than the other such that the ends of said tip portions are offset along the length of said tip portions, each of said jaws having an inner surface that abuts with the inner surface of the other jaw when said jaws clampingly abut, each of said jaws having an outer surface opposite its inner surface, the outer surface of the shorter tip portion being offset transversely to the length of said tip portions from the portion of the inner surface of the longer tip portion that extends beyond the end of said shorter tip portion.

2. The clamp of claim 1 wherein the free ends of said tip portions are rounded.

3. The clamp of claim 1 wherein each of said tip portions includes an abutting face, said faces being serrated and the serrations of one face being adapted to mate with the serrations of the other face.

4. The clamp of claim 3 wherein the region of the longer tip portion extending beyond the shorter tip portion is substantially smooth.

5. The clamp of claim 4 wherein the length of said region is approximately five millimeters.

6. An optic nerve clamp, comprising a pair of clamping jaws connected at a pivot or relative movement about a pivot axis extending through said pivot, each of said jaws having a tip portion on one side of said pivot and a handle portion on the opposite side of said pivot, said tip portions, arranged to clampingly abut with one another, being curved precisely sufficiently to allow access to the the optic nerve around the eyeball and extending out of the plane perpendicular to said pivot axis, one of said tip portions being shorter than the other such that the ends of said tip portions are offset along the length of said tip portions, each of said jaws having a inner surface that abuts with the inner surface of the other jaw when said jaws clampingly abut, each of said jaws having an outer surface opposite its inner surface, the outer surface of the shorter tip portion being offset transversely to the length of said tip portions from the portion of the inner surface of the longer tip portion that extends beyond the end of said shorter tip portion, the end of the longer tip portion being tapered sufficiently to allow said instrument to wedge between tissues which might otherwise interfere with access to the tissue desired to be clamped, said offset of said tip portions being adapted to permit the tissue desired to be clamped to be located between the end of said shorter tip portion and the section of said longer tip portion extending beyond said shorter tip portion.

7. The instrument of claim 6 wherein each of said tip portions includes an abutting face, said abutting faces being matingly serrated.

8. The instrument of claim 6 wherein the extension of the longer tip portion beyond the shorter tip portion has a face closest to said opposed tip portion which is substantially smooth.

9. The instrument of claim 8 wherein said extension is approximately five millimeters in length.

* * * * *

UNITED STATES PATENT AND TRADEMARK OFFICE
CERTIFICATE OF CORRECTION

PATENT NO. : 4,574,804
DATED : March 11, 1986
INVENTOR(S) : Badrudin Kurwa

It is certified that error appears in the above—identified patent and that said Letters Patent is hereby corrected as shown below:

Column 4, line 35, the word "or" should read "for".

Signed and Sealed this

Tenth Day of June 1986

[SEAL]

Attest:

Attesting Officer

DONALD J. QUIGG

Commissioner of Patents and Trademarks